United States Patent [19]

Bougard

[11] Patent Number: 4,596,235
[45] Date of Patent: Jun. 24, 1986

[54] HEATING APPARATUS

[76] Inventor: Jacques L. Bougard, Le Beaulieu, 44, 6140 Fontaine-L'Evêque, Belgium

[21] Appl. No.: 595,921

[22] Filed: Apr. 2, 1984

[30] Foreign Application Priority Data

Apr. 15, 1983 [BE] Belgium .................... PV 0/210569

[51] Int. Cl.⁴ .............................................. F24H 1/00
[52] U.S. Cl. ................................ 126/350 R; 126/355; 126/360 A
[58] Field of Search ............... 126/362, 355, 350 R, 126/350 B, 360 A, 359; 122/5.5 A; 159/4 B, 16 R, 16 A; 261/79 R, 98, 94, 115, 126, DIG. 72; 210/150

[56] References Cited

U.S. PATENT DOCUMENTS

| | | | |
|---|---|---|---|
| 884,223 | 4/1908 | Shipley | 126/359 |
| 2,878,644 | 3/1959 | Fenn | 126/360 A X |
| 3,648,682 | 3/1972 | Bougard | 126/359 |
| 3,692,017 | 9/1972 | Glachant et al. | 126/360 A |
| 3,826,240 | 7/1974 | Miyahara | 126/355 |
| 3,982,392 | 9/1976 | Crow | 431/173 X |
| 4,089,637 | 5/1978 | Smith et al. | 431/173 X |
| 4,275,708 | 6/1981 | Wood | 126/355 |

Primary Examiner—Randall L. Green
Attorney, Agent, or Firm—Scully, Scott, Murphy & Presser

[57] ABSTRACT

There is described a heating apparatus having a burner, a combustion chamber, means allowing to mix a primary fluid with the combustion gases, and means for containing a secondary fluid to be heated, which apparatus notably comprises means so arranged as to impart an annulus-like movement to the combustive gas-fuel mixture inside the combustion chamber, to obtain an uniform temperature in the whole chamber.

23 Claims, 4 Drawing Figures

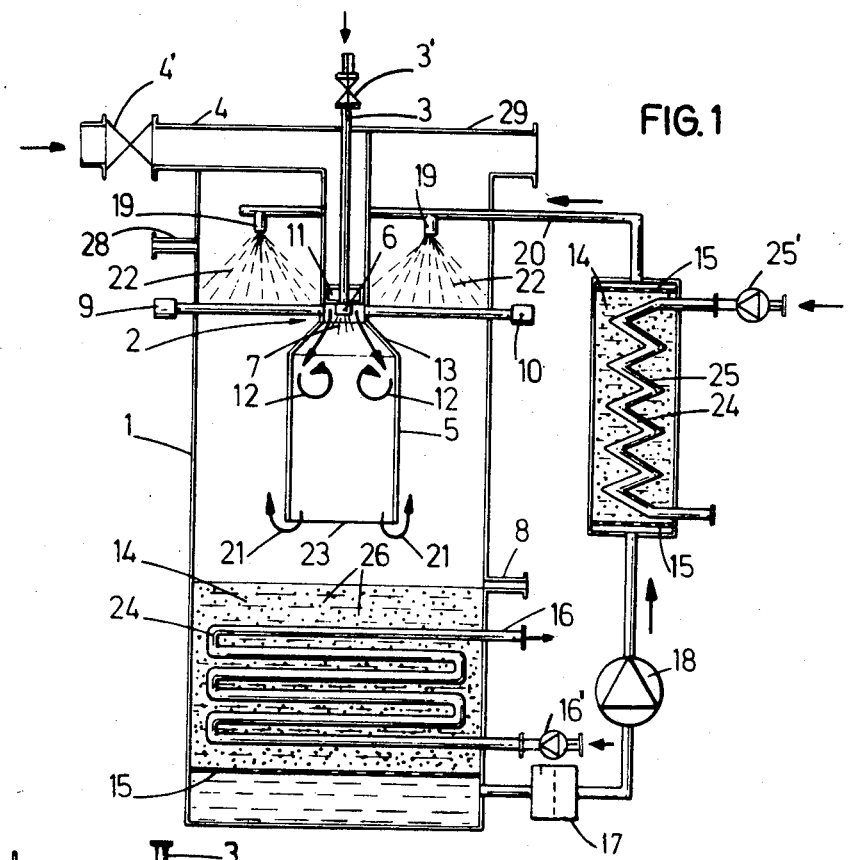
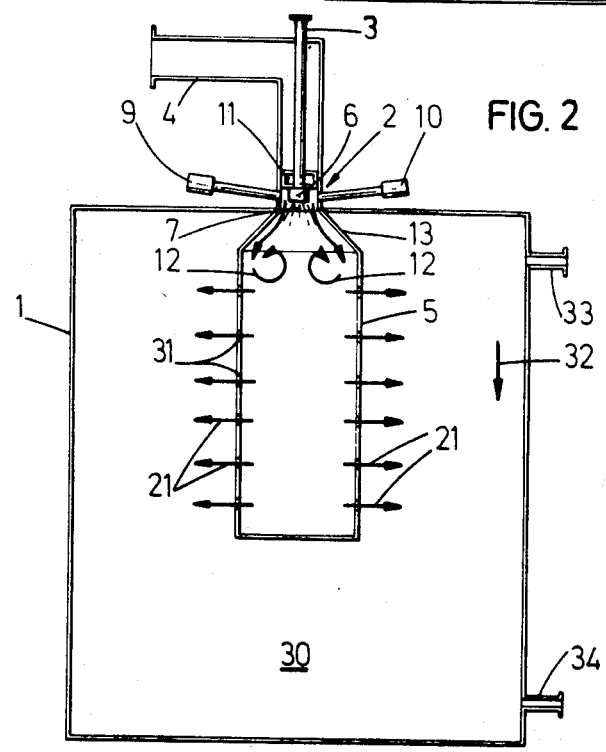

HEATING APPARATUS

BACKGROUND OF THE INVENTION

This invention relates to a heating apparatus which comprises a burner, a combustion chamber, means for obtaining the mixing of a primary fluid with the combustion gases, and means for containing a secondary fluid and for allowing after the mixing of the primary fluid with the combustion gases, a heat exchange between said primary fluid and the secondary fluid to be heated.

To minimize the very large exchange surface areas which are required in the conventional heating apparatus, various apparatus have been designed for directly heating water, which allow for the same heating power of the burner, to substantially lower the magnitude of said exchange areas. However, the combustion chambers which are partly cooled by the flowing of an inner or outer water film, thus have walls which are subjected to very high temperatures, which are impossible to cool efficiently, thus causing distortions, corrodings, scale-forming cracks and finally breaking-down of said walls. There results therefrom heavy maintenance costs and a relatively short life duration of the heating apparatus, even when use is made of noble materials for the manufacture thereof.

SUMMARY OF THE INVENTION

The invention has for object to obviate said drawback and to provide a fluid-heating apparatus which generates high heating powers inside a small volume, which has heating throughputs as reckoned on the low fuel heating power, much higher than 100%, and which insures at the same time the cleaning of the combustion products before discharging same in the atmosphere, said apparatus being very simple and quite cheap to manufacture, to operate and to maintain. The apparatus according to the invention is also particularly advantageous for central generating of hot water in agro-alimentary industries, for heating buildings at low temperatures through the ground, with radiators, convectors or batteries, for vaporizing liquefied gases such as natural gases, propane, butane, oxygen, and nitrogen.

For this purpose according to the invention, the apparatus comprises means so arranged as to cause an annulus-like movement of the combustive gas-fuel mixture inside the combustion chamber, to obtain a substantially uniform temperature inside the whole combustion chamber, and an enclosure so arranged about the combustion chamber as to contain a major portion at least of the primary fluid.

In an embodiment of the invention, the burner comprises a combustive gas feed pipe, and a fuel feed pipe which is co-axial and has a smaller cross-section relative to said gas feed pipe, leading to the combustion chamber, said fuel feed pipe having an injection head which is provided with directed nozzles the direction of which relative to the axis of said pipes varies by an angle between 15° and 90°.

In an advantageous embodiment of the invention, said means so arranged as to impart an annulus-like movement to the mixture of combustive gas and fuel inside the combustion chamber are comprised of a fixed screw which is mounted on said fuel feed pipe, said screw lying adjacent to said injection head and somewhat higher than said head.

In a particularly advantageous embodiment of the invention, the combustion chamber is cylinder-shaped, the diameter thereof being 1.6 to 6 times the diameter of the combustive feed pipe, the top portion of said chamber being of truncated-cone shape.

In an embodiment of the invention, the primary fluid is a liquid and the heating apparatus comprises at least one opening lying in the lower portion of the combustion chamber to let the combustion gas out, and injection members to atomize said liquid into the combustion gases so as to obtain said mixture, which members are arranged inside said enclosure and lie above and outside the combustion chamber to allow on the one hand a heat exchange between the combustion gases flowing out of the chamber and rising inside the enclosure, and the atomized liquid moving down inside the enclosure over a major length of the chamber at least, and on the other hand an efficient cooling of the combustion chamber walls, the enclosure provided to collect the atomized liquid having an outlet opening for said liquid.

In an advantageous embodiment of the invention, means are provided inside the combustion chamber on the one hand to enhance the heat exchange between the combustion gases and the walls of said chamber, and on the other hand to retain a major part at least of the molten residue materials originating from the combustion, said means being preferably comprised of fins which are regularly distributed over the inner circumference of the chamber, substantially at right angle to the lengthwise axis of said chamber.

In a particularly advantageous embodiment of the invention, the heating apparatus comprises means to control the temperature of the combustion chamber walls, said means being comprised of a casing which is arranged sidewise about the combustion chamber, casing inside which flows a cooling liquid, said casing having over the major portion of the combustion chamber circumference at least, a common wall therewith.

In another embodiment of the invention, the primary fluid is a gaseous fluid and the heating apparatus enclosure comprises an inlet opening and an outlet opening to let the gaseous fluid flow in and out of said chamber as well as a series radial nozzles which are regularly distributed over the combustion chamber circumference and over a major length of said chamber, the lengthwise axis of said nozzles lying substantially at right angle to the combustion chamber axis, said nozzles being so arranged as to let the combustion gases escape, to insure said mixing of the combustion gases with the gaseous fluid, and to allow a heat exchange between said combustion gases and the gaseous fluid flow inside the enclosure, the inlet and outlet openings being so arranged in the enclosure as to have the combustion gases be ejected along directions substantially at right angle to the gas flow therein.

The apparatus also has for advantage relative to the previous devices to be usable not only with gas-like fuels, such as the natural gases and the production gases, but also with liquid fuels, such as light oils, residue oils or paper-work washes, with atomized and dried solid fuels such as wood, rich or blazing coals, lignites or peats, and also with finely atomized solid fuels in admixture with liquids, such as rich coal-water-oil or blazing coal-water mixtures, all such fuels being substantially less expensive than natural gases. As it has been noted, the apparatus according to the invention also allows to clean the combustion products before discharging same into the atmosphere, and notably to lower the proportions of fly ashes and sulfur dioxide below limits imposed by various local or national laws. The apparatus according to the invention has also for advantage relative to the known apparatus of this kind, to be usable not only with complete combustion products but also with part-combustion products, that is as a gas-generator where the sensitive heat of the combustion products might be recovered.

BRIEF DESCRIPTION OF THE DRAWINGS

Other details and features of the invention will stand out from the following description, given by way of non limitative example and with reference to the accompanying drawings, in which:

FIG. 1 is a diagrammatic view in elevation and in section, showing an embodiment of a heating apparatus according to the invention.

FIGS. 2 and 3 are views similar to FIG. 1, showing variations of the heating apparatus as shown in FIG. 1.

DESCRIPTION OF THE INVENTION

Figure 1A:
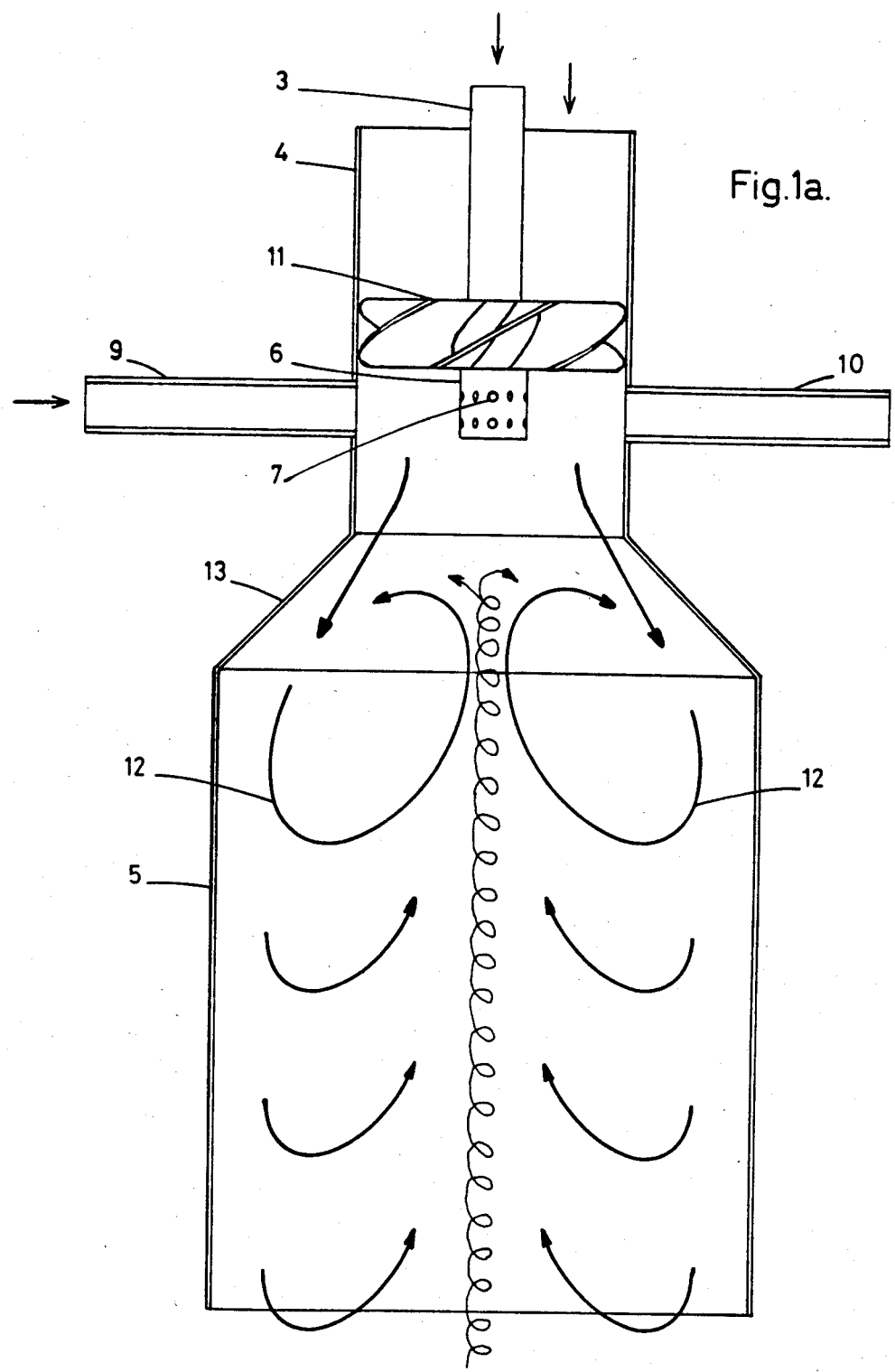
FIG. 1a is a diagramatic view in elevation of the burner and combustion chamber.

In the various figures, the same reference numerals pertain to similar or identical elements.

The heating apparatus according to the invention, as shown in FIG. 1, is intended for heating a fluid and comprises an enclosure 1, a burner 2 fed through a pipe 3 with a flow control valve 3' with pressurized gaslike fuel or with liquid or solid fuel, or else with a liquid-solid mixture in the shape of fine particles suspended in a fast stream of so-called primary combustive gas, which is insufficient to reach the flaming limits, and fed through a pipe 4 with a flow control valve 4' with a so-called secondary combustive gas, which is sufficient to insure the complete combustion, as well as a combustion chamber 5 arranged co-axially inside enclosure 1.

The fuel feed pipe 3 with a crosssection smaller than the combustive medium feed pipe 4 and arranged co-axially therein, comprises an injection head 6 provided with directed nozzles 7 (FIG. 1a), the direction of which relative to the axis of said pipes 3 and 4 varies by an angle between 15° and 90°. The burner 2 further comprises two horizontal tubes arranged level with said injection head 6, in diametrically-opposed positions on pipe 4, the first tube being used for the passage of a high-voltage spark-plug or an intermittent ignition pilot burner 9, in accordance with various national regulations, and the second tube being used for arranging a photocell 10 allowing to monitor the flames generated by the burner 2. A fixed screw 11 is mounted on the fuel feed pipe 3 adjacent to the injection head 6 and slightly above same (FIG. 1a). Said screw 11 is so arranged as to impart an annulus-like movement 12 to the combustive gas-fuel mixture inside combustion chamber 5 to obtain a substantially uniform temperature inside the whole combustion chamber. Said screw 11 does not only allow avoiding high temperature differentials inside the combustion chamber and thus causing a fast damaging thereof, but also obtaining a more complete combustion than with apparatus of the same kind as known up to now, the combustive medium-fuel mixing being made much more efficiently than in said known apparatus. Said screw 11 is actually so arranged as to cause a fast rotating of the gaseous combustive medium and the fuel fed to combustion chamber 5, so as to maintain inside the top part thereof, high-speed recycling annulus-like streams, to obtain a fast and complete combustion inside a very small volume, and to obtain a substantially uniform temperature inside the whole combustion chamber. The generating of such annuluslike streams is made easier due to the specific shape of the combustion chamber the top portion of which is in the shape of a truncated cone 13 the apex angle of which varies from 30° to 90°. The diameter of the cylinder-like combustion chamber which is arranged co-axially inside the enclosure 1, is 1.6 to 6 times the diameter of the combustive gas feed pipe 4.

The bottom portion of enclosure 1 contains a liquid bath 14, called hereinafter "primary liquid", comprising the heat-transfer liquid which is most often comprised of a solution the highest level of which is determined by an overflow 8, and in which a heat exchanger 16 is possibly dipped. The primary liquid 14 is sucked from the bottom of enclosure 1 through an automatic filter 17 which is provided with a periodic-drain opening, for separating the fly-ashes which are possibly formed by the combustion, the liquid being forced thereafter under high pressure by a pump 18 towards atomizers 19 which are mounted on a feed pipe 20 in the enclosure top part, above and outside the burner-combustion unit. Said atomizers 19 which number at least four, are arranged about the feed pipe 4 for the combustive gas and face downwards to project the primary liquid 14 in a cone-shaped spray 22 over the burner-combustion chamber unit 2,5 and into the combustion gases 21 leaving the chamber and rising inside the enclosure. The axis of the cone-shaped spray 22 lies in parallel relationship with the lengthwise axis of the combustion chamber. As it flows down, the atomized primary liquid is warmed up on the one hand by contacting the outer walls of combustion chamber 5, and on the other hand by contacting directly in counter-flow combustion gases leaving through opening 23 and rising inside the enclosure. The warmed-up primary liquid then drops in the bottom part of enclosure 1 and abandons the heat thereof to some fluid 24, called hereinafter "secondary fluid", such as a gas, steam, liquefied gas to be atomized, atomized or grain-like liquid or solid, flowing in counter-current inside the heat-exchange coil 16, or inside a heat-exchange coil 25 lying outside enclosure 1, which dips completely into the primary liquid 14, said primary fluid then being cycled-back to the atomizers 19 located at the top of said enclosure. The counter-current flow of the fluid is provided by a circulating pump 16' for coil 16 and a circulating pump 25' for pump 25 with the arrows indicating the inlet and outlet directions of the fluids. As shown in FIG. 1, said atomizers 19 are arranged inside the enclosure in such a way as to let the atomized primary liquid mix with the combustion gases over the whole length of the combustion chamber and in such a way as to have the chamber walls perfectly cooled over all the surface area thereof, which allows avoiding the formation of badly-cooled zones, thus markedly hotter zones which are more sensitive to distortion or damaging.

According to the invention, all kinds of heat exchangers may be used, that is smooth-tubes, fin-tubes, plates, etc., but the primary liquid in which such exchangers will be dipped will preferably comprise solid particles 26 with a specific weight which is lighter or heavier than the specific weight of the primary liquid 14 along the flow direction thereof, that is depending on a falling or rising flow, for example granulates from plastic material, sand grains, porcelain balls or glass balls, which are retained in stable suspension or fluidizing in the primary liquid stream surrounding the heat exchanger through which flows the secondary fluid. The slight impacts and frictions of the particles 26 on the heat exchanger walls avoid the settling of impurities, retain the exchange surfaces absolutely clean and smooth, substantially increase the heat-exchange factors between the primary bath and the clean surfaces, while causing but a negligible metal eroding. Grids 15 retain the particles 26 inside the heat-exchange zone.

It has been noted that the heat-exchange factor between a water stream without suspended particles and a metal wall was $450 \text{ W} \times \text{m}^{-2} \times °\text{C}.^{-1}$, while such factor rises to $3410 \text{ W} \times \text{m}^{-2} \times °\text{C}.^{-1}$ for the same water stream with fluidizing particles. The use of such particles appears of particular importance when vaporizing liquefied gases flowing through heat-exchange tubes. In a conventional heat exchanger with water bath or streaming, it is very difficult to avoid ice being formed on the tubes the temperature of which goes down to $-170°$ C. in some zones. There results thus therefrom a very bad heat conducting and a lowering of the efficiency. To the contrary, in the apparatus according to the invention, the stirring by fluidizing prevents icing, which in combination with high heat-exchange factors, makes the apparatus very advantageous for such use.

The heat efficiency of the heating operation is a function of the fuel and combustive medium nature, of the excess or lack of combustive medium relative to the stoechiometric amount, of the outlet temperature of the combustion products which is very near the inlet temperature of the primary liquid in the enclosure or of the secondary fluid in the exchanger, and finally of the pressure of the combustion products in the enclosure. With a given fuel and combustive medium excess, the heat efficiency increases as the outlet temperature of the combustion products goes down or as the pressure of said products rises.

The most advantageous applications of the apparatus according to the invention lie where the inlet temperature of the secondary fluid in the exchanger is lower than about 50° C., so as to obtain under atmospheric pressure, an outlet temperature for the combustion products lower than 58° C. for example for natural gas on the basis of methane, burned with a 12% air excess, or else at 56° C. for atomized wood with 15% water, burned with a 12% air excess. In this case, the amount of steam from the combustion which is in excess relative to that amount which corresponds to saturation, condenses in the primary water bath. There is thus a material transfer in the direction of the combustion products-bath, and the excess volume of the primary bath which corresponds to such condensed water production will be discharged to waste by overflow through channel 8. The heat transfer makes use of the latent heat from the water condensing and consequently that heat corresponding to the steam excess which is condensed, is recovered. There results therefrom that the combustion efficiency and consequently the heating efficiency as reckoned on the lower heat power of the fuel, because the apparatus losses due to radiating and convection are to be neglected, lie higher than 100%, which corresponds to more than 90% as reckoned on the higher heat power of the fuel.

There will be given hereinafter by way of example, the operating conditions of a mains water re-heater according to the invention, intended for central producing of hot water in a slaughter house, as substitute for a conventional steam boiler:

Nominal heat power at the inlet on the basis of the higher heating value: 1163 kW=1000 Mcal/h.
Higher heating value of natural gas: 15.456 kWhS/kg.
Natural gas flow rate: 75.25 kg/h.
Air excess: 10%.
Nitrogen flow rate in combustive air: 1094.7 kg/h.
Oxygen flow rate in combustive air: 330.4 kg/h.
Temperature of combustive air and natural gas: 15° C.
Combustive air pressure at the inlet to the burner: 1050 mb.
Steam proportion in dry air: 5 gr/kg dry air.
Steam flow rate in combustive air: 7.1 kg/h.
Re-heated secondary water flow rate: 24,938 kg/h.
Secondary water temperature at the inlet to exchanger: 10.5° C.
Secondary water temperature at the outlet from exchanger: 50.2° C.
Temperature differential for secondary water: 39.7° C.
Nominal heat power at the outlet: 990 Mcal/h=1151 kW.
Nominal heat efficiency based on higher heat value: 99.0%.
Outlet temperature of the combustion products: 24.0° C.
Nitrogen flow rate in the combustion products: 1094.7 kg/h.
Carbon dioxide flow rate in the combustion products: 206.6 kg/h.
Oxygen flow rate in the combustion products: 30.0 kg/h.
Steam flow rate in the combustion products: 25.3 kg/h.
Primary water nature: city mains water without addition.
Condensed water flow rate to waste: 143.8 kg/h.
Primary water flow rate in the pump: about 25,000 kg/h.
Primary water temperature at the inlet to exchanger: 62.0° C.
Primary water temperature at the outlet from exchanger: 22.3° C.
The heat efficiency based on the lower heating value of the natural gas has risen from 65% in a conventional boiler to 109.9% with the apparatus according to the invention and the capital costs will be amortized in less than one year with the savings obtained on the fuel consumption.

In other applications of the apparatus according to the invention, for instance the conventional heating of buildings with radiators, with modulation of the outgoing temperature according to the outside temperature, the inlet temperature for the secondary water in the exchanger might be higher than 50° C. and reach 55° C. during the winter months. To retain a heat efficiency higher than 100% based on the lower heating value of clean fuel gases, a first method lies in increasing the pressure of the combustion products inside the enclosure by mounting a supercharger for combustive medium and fuel on the inlet, and a recovery turbine on the outlet. Another method lies in substituting to the primary water an aqueous solution of inorganic or organic compounds, for example potassium carbonate, which do not undergo any decomposition, polymerizing, nor any change of the properties thereof when contacting combustion products at high temperatures, and which have a low viscosity in the use temperature range and a boiling point at atmospheric pressure much higher than 100° C. In such a case, up to a temperature about 75° C. under atmospheric pressure, the amount of steam from the combustion which is in excess relative to that amount which corresponds to saturation, condenses in the primary bath and cause diluting thereof. The primary bath volume may be retained constant by separating the condensed water by means of a known method, for example reverse osmosis, with a relatively low energy comsumption.

As already stated hereinabove, the apparatus according to the invention also allows to clean the combustion products, before discharging same in the atmosphere. Such an object is obtained without special equipment, such as dust-catcher or washer, and by simply adding to the primary aqueous solution, substances which can bind noxious materials such as sulfur and fly ashes, for example neutralizers, such as sodium carbonate, potassium carbonate, caustic soda or caustic potash. More than 90% of those sulfites and sulfates being formed by the reactions go into solution in the primary bath and are discharged to waste together with the condensed water. Such neutralizers may be added to the primary bath, through pipe 28. The cooled and cleaned combustion gases are then discharged to the atmosphere through pipe 29.

The heating apparatus according to the invention as shown in FIG. 2, differs from the apparatus as shown in FIG. 1, due to the primary fluid being used for this purpose being a fluid in gas or vapour form. It does comprise inside an enclosure 1 containing the gaseous fluid 30, a burner 2 fed through pipe 3 with pressurized gas fuel or with liquid and solid fuel in the form of fine droplets suspended in a fast flow of so-called secondary combustive gas, as well as a combustion chamber 5. The burner-chamber 2,5 is formed by elements similar to the burner-chamber 2,5 from the apparatus as shown in FIG. 1, that is essentially by a combustive medium feed pipe 4, a fuel feed pipe 3, a screw 11, an injection head 6 provided with nozzles 7, and a combustion chamber proper 5. However the combustion chamber is provided with a series radial nozzles 31 which are regularly distributed on the chamber circumference and over the whole length thereof, the lengthwise axis of said nozzles lying at right angle to the combustion chamber axis. Actually, said radial nozzles 31 let escape streams of combustion products or gases 21 at high temperature, along directions at right angle to the primary gaseous fluid stream 30, or adjacent to such positions, the direction of said gaseous stream being shown by arrow 32. The falling gaseous stream entering the enclosure through opening 33 and leaving same through opening 34, is heated on the one hand by the direct contact with the combustion chamber walls, and on the other hand, by the direct contact with the streams of hot burned gases 21. There results therefrom a very fast homogeneizing of the temperatures in the whole enclosure volume, without generating therein special load losses. The outer heat exchanger containing the secondary fluid to be heated is similar and located in a similar way to the heat exchanger 25 of the heating apparatus as shown in FIG. 1. There is of course no atomizer as the primary fluid is a gas . One might naturally also provide for a circulation of the primary gaseous stream 30 along a direction at right angle to the combustion chamber axis.

Figure 3:
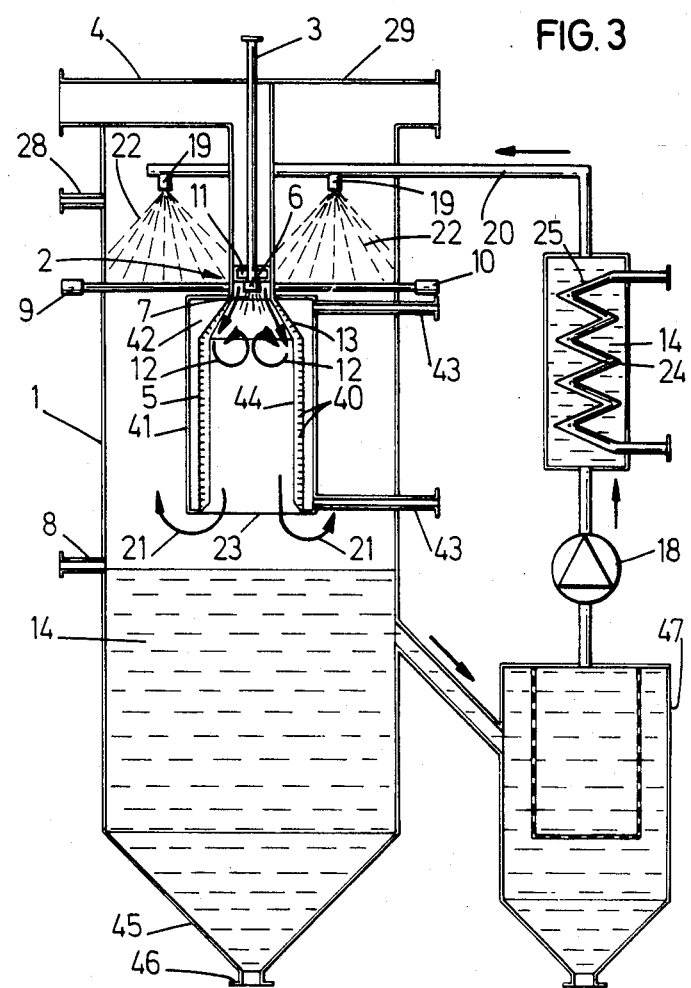

The heating apparatus according to the invention as shown in FIG. 3, differs essentially from the heating apparatus as shown in FIG. 1, by the structural form of the combustion chamber 5 thereof. Indeed, the combustion chamber of the heating apparatus in FIG. 3 is provided with fins 40 which are evenly distributed over the inner circumference thereof. Said fins 40 which lie at right angle to the chamber lengthwise axis, do actually enhance the heat exchange between the combustion gases and the walls of combustion chamber 5, and retain a substantial proportion of the molten ashes from the combustion. A co-axial cylinder-shaped casing 41 arranged sidewise about the combustion chamber and against same, in which a cooling fluid 42 flows, is used to control the temperature of the combustion chamber side walls, lower and upper tubes 43 allowing the fluid 42 to flow in the casing 41.

The fast rotating of the combustive medium-fuel mixture by screw 11 from burner 2, causes in the top portion of combustion chamber 5, annulus-shaped recycling streams 12 at high speeds, as in the case of the apparatus in FIGS. 1 and 2, to obtain a fast and complete combustion inside a small volume. The major proportion (about 90%) of the molten ashes formed by the burned solid fuels is thrown under the action of aerodynamic currents, on the inner walls of the combustion chamber, to first form a solidified insulating brittle layer 44, which is retained by the fins 40, then a viscous plastic intermediate layer, and finally a markedly liquid film which flows down under the combined action of the aerodynamic currents and gravity, the total thickness of said three layers being in the range of 20 mm. The remaining proportion of the ashes (about 10%) is carried along by the combustion gases. The control of the heat flow and the combustion wall temperature is essential to prevent the formation of ripples, rings or other surface irregularities on the combustion chamber, which lower the quality of the combustion and increase the carrying of ashes. As in the case of the apparatus shown in FIG. 1, the enclosure 1 contains in the lower part thereof, a primary liquid bath 14, which is preferably comprised of an aqueous solution the highest level of which is determined by the overflow 8. The molten ashes fall in said bath where they undergo a tempering and a breaking-down into grains with a size of a few millimeters, said grains then moving to the cone-shaped bottom 45 of the enclosure and settling thereon. The grains are then removed through the periodic-draining opening 46. The primary liquid is sucked at the enclosure bottom into a fine-ash separator in a way known per se, for example a fast decanter with sloping sheets, or an automatic filter with periodic-drain opening 47, and forced under high pressure by pump 18 through the counter-flow heat exchanger 25, towards the atomizers 19 mounted in the top part of the enclosure, above the combustion chamber 5. The primary liquid 14 atomized downwards in the enclosure is heated during the fall thereof, on the one hand by the contact with the outer walls of the combustion chamber, and on the other hand, by the direct contact in counter-flow with the combustion gases 21 leaving the combustion chamber through opening 23 and rising inside the enclosure. The primary liquid then abandons the heat thereof to some secondary fluid flowing through the heat exchange coil 25 and flowing in counter-current. As in the case of the apparatus shown in FIG. 1, to neutralize the sulfurous and sulfuric anhydrids from the combustion products, one of the above-mentioned neutralizers will be added to the primary liquid, through pipe 28. The cooled cleaned combustion gases are discharged to atmosphere through tube 29.

It must be understood that the invention is in no way limited to the above embodiments and that many changes may be brought therein without departing from the scope of the invention as defined by the appended claims.

For instance, it might naturally be possible to design heating apparatus having a plurality of burners and corresponding combustion chambers, and a series of atomizers arranged above said chambers on one or a plurality of levels and along any direction relative to the chamber axes. On the other hand, the secondary fluid to be heated as well as the primary fluid, whether a liquid or a gas, preferably also flows under pressure and in a closed circuit.

I claim:

1. A heating apparatus comprising:
   an enclosure having a burner and a combustion chamber mounted therein, said combustion chamber having at least one bottom opening lying in a lower portion of the combustion chamber, said burner including a combustion gas feed pipe and a fuel feed pipe leading to the combustion chamber for providing a combustion-gas fuel mixture inside the combustion chamber, said fuel feed pipe being co-axial with and having a smaller cross-section relative to said gas feed pipe, said burner including means for igniting said combustion-gas fuel mixture,
   an injection head mounted to the fuel feed pipe having directed nozzles for directing fuel into the combustion chamber at angles relative to the axis of the fuel feed pipe of between 15° and 90°,
   means for causing an annulus-like movement of the combustive gas-fuel mixture inside the combustion chamber including a fixed screw mounted on said fuel feed pipe within said combustive gas feed pipe and lying adjacent and above said injection head, to obtain a substantially uniform temperature inside the whole combustion chamber,
   means for obtaining the mixing of a primary fluid with the combustion gases leaving the combustion chamber through the bottom opening, including injection members to atomize said primary fluid into the combustion gases so as to obtain said mixture, said injection members being arranged inside said enclosure and lying above and outside the combustion chamber to allow a heat exchange between the combustion gases flowing out of the chamber and rising inside the enclosure and the atomized primary fluid moving down inside the enclosure over a major length of the chamber at least, and to allow an efficient cooling of the combustion chamber walls, the atomized primary fluid being collected in a bottom portion of the enclosure having an outlet opening for said primary fluid, and
   means for containing a secondary fluid and for allowing, after the mixing of the primary fluid with the combustion gases, a heat exchange between said primary fluid and the secondary fluid to be heated.

2. Heating apparatus as defined in claim 1, in which the combustion chamber and the enclosure are co-axial.

3. Heating apparatus as defined in claim 1, in which the combustion chamber is cylinder-shaped, the diameter thereof being 1.6 to 6 times the diameter of the combustive gas feed pipe, the top portion of said chamber being of truncated-cone shape.

4. Heating apparatus as defined in claim 1, in which the burner includes means for monitoring the flames from said burner, and wherein said ignition means and said flame controlling means both being arranged level with said fluid injection head.

5. Heating apparatus as defined in any one of claims 2, 3 or 4, including means for causing the secondary fluid to flow in counter-current to the primary fluid.

6. Heating apparatus as defined in claim 1, in which the primary fluid is a liquid.

7. Heating apparatus as defined in claim 6, in which the injection members include at least four atomizers arranged about the combustive gas feed pipe, said atomizers each being so arranged as to throw liquid on the combustion chamber and in the combustion gases as they rise inside the enclosure in a cone-shaped spray the axis of which lies substantially in parallel relationship with the lengthwise axis of the combustion chamber.

8. Heating apparatus as defined in claim 7, in which said atomizers are so arranged inside the enclosure as to have the atomized liquid mix with the combustion gases over the whole length of said combustion chamber, and in such a way as to have the combustion chamber walls cooled over the whole surface area thereof.

9. Heating apparatus as defiend in claim 6, which further includes an overflow which retains the liquid inside the enclosure at a constant level in the bottom portion thereof.

10. Heating apparatus as defined in claim 9, in which said means for containing the secondary fluid and for allowing a heat exchange between said primary liquid and said secondary fluid to be heated includes a coil which is so arranged as to be completely immersed in the primary liquid which is contained in the enclosure bottom portion thereby forming a heat exchange zone, the fluid inside the coil flowing counter-current to said liquid.

11. Heating apparatus as defined in claim 10, in which the primary liquid in the heat exchange zone thereof with the fluid to be heated, contains solid particles lying in fluidizing condition in a liquid stream, said particles increasing the heat exchange between the liquid and the fluid, and said zone includes screens retaining the particles inside said zone.

12. Heating apparatus as defined in claim 11, in which the solid particles are comprised of granulates from plastic material, sand grains, porcelain or glass marbles, or mixtures of such materials.

13. Heating apparatus as defined in claim 9, which further comprises a chamber outside the enclosure, which is so arranged as to contain part of said primary liquid, communicating with the enclosure bottom portion, and a means for containing a third fluid and for allowing a heat exchange between said liquid and said third fluid to be heated includes a coil which is so arranged as to be completely immersed in the liquid in the outer chamber, the third fluid inside said coil flowing counter-current to said liquid.

14. Heating apparatus as defined in claim 9, which further comprises means for separating the residual solids of the combustion from that liquid contained in the enclosure bottom portion, said means lying outside said enclosure and upstream of the outlet for said liquid.

15. Heating apparatus as defined in claim 14, in which the enclosure bottom is cone-shaped to make settling of the residual solids with the largest volume easier.

16. Heating apparatus as defined in claim 6, in which means are provided inside the combustion chamber on the one hand to enhance the heat exchange between the combustion gases and the walls of said chamber, and on the other hand, to retain at least a major part of molten residue materials originating from the combustion, said means being preferably comprised of fins which are regularly distributed over the inner circumference of the chamber, substantially at right angle to the lengthwise axis of said chamber.

17. Heating apparatus as defined in claim 6, which further comprises means for controlling the temperature of the combustion chamber side walls.

18. Heating apparatus as defined in claim 17, in which said means for controlling the temperature of the combustion chamber side walls includes a casing which is arranged sidewise about the combustion chamber, inside which flows a cooling liquid, said casing having over the major portion of the combustion chamber circumference at least, a common wall therewith.

19. Heating apparatus as defined in claim 6, in which the primary liquid which will form said primary fluid mixture with the combustion gases, flows in closed circuit inside said apparatus.

20. Heating apparatus as defined in claim 6, in which said primary fluid flows in closed circuit.

21. Heating apparatus as defined in claim 6, in which the primary liquid and said secondary fluid are selected from the group which comprises water and the inorganic or organic aqueous solutions.

22. Heating apparatus as defined in claim 6, in which the primary liquid and said secondary fluid are pressurized.

23. Heating appparatus as defined in claim 6, in which the liquid contains substances which can bind noxious substances such as sulfur, ashes, etc.

* * * * *